United States Patent [19]

Sheppard et al.

[11] Patent Number: 5,191,015

[45] Date of Patent: Mar. 2, 1993

[54] POLYMERS AND POLYMER-PEPTIDE CONJUGATES

[75] Inventors: Robert C. Sheppard, Cambridge; Peter Goddard, West Sussex, both of England

[73] Assignee: Medical Research Council, London, United Kingdom

[21] Appl. No.: 476,393

[22] PCT Filed: Dec. 9, 1988

[86] PCT No.: PCT/GB88/01090

§ 371 Date: Jun. 4, 1990

§ 102(e) Date: Jun. 4, 1990

[87] PCT Pub. No.: WO89/05305

PCT Pub. Date: Jun. 15, 1989

[30] Foreign Application Priority Data

Dec. 9, 1987 [GB] United Kingdom ................ 8728752
Jun. 25, 1988 [GB] United Kingdom ................ 8815170

[51] Int. Cl.[5] .......................... C07K 1/04; C07K 17/08
[52] U.S. Cl. .............................. 525/54.1; 525/54.1; 530/333; 530/334; 530/338

[58] Field of Search .............. 525/54.1; 530/333, 334, 530/338

[56] References Cited

U.S. PATENT DOCUMENTS

| 3,700,609 | 10/1972 | Tregear et al. | 525/54.1 |
| 3,737,412 | 6/1973 | Wildi | 530/334 |
| 4,598,122 | 7/1986 | Goldenberg | 525/61 |
| 4,923,901 | 5/1990 | Koester et al. | 536/28 |

OTHER PUBLICATIONS

Webb et al., JCS Perkin I, 1962, 125, pp. 4307-4319.
Arshady et al., JCS Perkin I, 1981, 538, pp. 529-537.
Dryland et al. J. Chem. Soc. Perkin I 1986 pp. 125-137.

*Primary Examiner*—Nathan M. Nutter
*Assistant Examiner*—Jeffrey Culpeper Mullis
*Attorney, Agent, or Firm*—Nixon & Vanderhye

[57] ABSTRACT

New polymer supports containing cleavable cross-links are described which are suitable for solid phase peptide synthesis and can then be solublized for further chemical or biological manipulation (including immunization) in solution.

26 Claims, 5 Drawing Sheets

POLYMERS AND POLYMER-PEPTIDE CONJUGATES

This invention relates to insoluble polymer supports for use in peptide synthesis, to their use in peptide synthesis, and polymer-peptide conjugates.

It is known to use polymers as insoluble support matrices in peptide synthesis, oligonucleotide synthesis, oligosaccharide synthesis, catalysis applications, affinity chromatography, pharmaceutical applications and for enzyme immobilisation. The use of insoluble polymers as reagent supports in organic syntheses facilitates the separation of products and reagents and has other advantages.

The use of insoluble polymer supports has been of particular importance in the synthesis of peptides (see for example the Merrifield synthesis—Merrifield, R.B. (1962), Fed. Proc. Fed. Amer. Soc. Exp. Biol., 21, 412 and (1963), J. Amer. Chem. Soc., 85, 2149) and oligonucleotides (see for example Letsinger, R.L. and Kornet, M.J. (1963), J. Amer. Chem Soc., 85, 3045 and (1964), J. Amer. Chem. Soc., 86, 5163). The solid phase synthesis of peptides has been reviewed by a number of authors (see Meienhofer, J., (1973) in "Hormonal Proteins and Peptides", Ed. C.H. Li, 2, 45–267, Academic Press, New York; Erickson, B.W. et al (1976) in "The Proteins", Ed. H. Neurath et al, 2, 255–327, Academic Press, New York; and Barany, G. and Merrifield, R.B. (1980) in "The Proteins", Ed. E. Gross et al 3–284, Academic Press, New York).

The classical Merrifield method of polymer supported peptide synthesis was developed using insoluble cross-linked polystyrene supports. The supports are prepared by copolymerising divinylbenzene and styrene in suspension, to produce an insoluble beaded polymer. The peptide is synthesised on the insoluble support which facilitates separation of the desired produce (attached to the support) from the other reagents (in solution) and has other advantages. The polystyrene backbone remains largely chemically inert, although as the peptide chain grows, the swelling properties of the polymer may alter.

A development of the Merrifield method was proposed by Sheppard (Sheppard, R.C. (1971), in "Peptides 1971", Ed. H. Nesvadba, 111–125, North Holland, Amsterdam; Atherton, E., Clive, D.L.J., and Sheppard, R.C. (1975) J. Amer. Chem. Soc 97 6585) in which the non-polar polystyrene is replaced with a polar polymer, polydimethylacrylamide. Polydimethylacrylamide possesses similar solvation properties in polar solvents to those of a side chain protected peptide chain synthesised on the polymer. This minimises aggregation phenomena within the peptide-polymer matrix and may result in improved peptide quality and yield. The use of polydimethylacrylamide as a polymer support has been reviewed by Atherton et al (Atherton, E. et al (1979) Biorg. Chem., 8, 370. Peptide synthesis on insoluble cross-linked polydimethylacrylamide gels obtained by copolymerisation of dimethylacrylamide, acryloylsarcosine methyl ester and ethylene bisacrylamide is well established (Atherton E. et al, (1979) Biorg. Chem., 8, 351). Alternative polyamide supports have been described (Smith, C.W. et al (1979), Int. J. Peptide. Protein. Res., 13, 109; Stahl, G.L. et al (1979), J. Amer. Chem. Soc., 101, 5383; and Epton R. et al (1979), Polymer, 20, 1444). The polydimethylacrylamide resin has been prepared by suspension copolymerisation and used as a beaded gel in a batch process peptide synthesis (Arshady, R. et al, (1979). J.C.S., Chem. Comm., 423). More recently, copolymerisation of the monomers in the presence of an inert Kieselguhr support matrix has enabled the polymer support to be packed into a column and used in a continuous flow method of peptide synthesis (Atherton, E., Brown E., Sheppard, R.C., and Rosevear, A. (1981) J. Chem. Soc. Chem. Comm., 1151; Sheppard, R.C. (1983), Chem. Brit., 19, 402).

Peptides have been synthesised on "soluble polymer supports, such as polyethyleneglycol, to form a polymer-peptide conjugate molecule. Precipitation of the polymer-peptide conjugate by changing the solvent has been used to facilitate separation of the conjugate from by-products (Mutter et al, (1978) Angew. Chem. Int. Edn., 13, 88).

An important application of peptide synthesis is the preparation of synthetic immunogens for use as vaccines. It has been established (Armon. R., (1980) Amer. Rev. Microbiol., 34, 593) that some peptides are able to elicit antisera capable of binding to a virus or bacteriophage in vitro. For further teaching reference may be made to "Synthetic Peptides as Antigens", Eds R. Porter and J. Whelan, CIBA Symposium 199, Wiley and Sons, Chichester, UK, 1986. The peptide may, for example, mimic a distinctive antigenic determinant on a particular protein of interest. Vaccines to foot-and-mouth virus, polio virus, influenza virus and hepatitis B virus are all currently under investigation by various groups, based upon the use of synthetic peptides produced by solid phase synthesis. Synthetic vaccines have the advantage that they may produce fewer side effects and be safer than existing vaccines based on inactivated virus.

In general, however, short peptides alone are not capable of eliciting an immune response, even though they may be antigenic and capable of binding to specific antibodies. For use as an immunogen or inoculant, the peptide is linked covalently to a large carrier molecule which is itself immunogenic. Proteins are widely used as carrier molecules and bovine serum albumin, chicken ovalbumin and keyhole limpet haemocyanin are three such proteins which have been used to raise antibodies to synthetic antigens in experimental animals. The reactions necessary to link covalently a peptide to a large proteinaceous carrier may be inefficient as a result of numerous side reactions, depending on the functional groups which are used to form the linkage. Moreover, the homogeneity of the linked product can only be determined with difficulty, leading to quality control difficulties.

Conventionally, therefore, in order to prepare a synthetic polypeptide suitable for use as a vaccine by the solid-phase method, it is necessary to prepare first the peptide on an insoluble polymer support, to cleave the synthetic peptide from the support, and to bind convalently the peptide to a soluble carrier. In the alternative, using classical solution phase techniques of peptide synthesis, it is necessary to bind covalently the peptide to a soluble carrier. These steps all necessarily reduce the overall yield and the purity of the final product.

It has been suggested to prepare a peptide on an insoluble polymer support and then to disintegrate the polymer with ultrasound to produce a material suitable for inoculation (Bahraohi, E. et al, "Proceedings of the 18th European Peptide Symposium" (1984), 165–168).

In the unconnected field of gel electrophoresis, problems of product recovery have been solved by the design of gels which may be solubilised. Gel electrophoresis relies upon the different migration speeds of various components of a sample through a gel, under the influence of an applied electric field, to separate the components. The separated components may be detected on the gel as a first step to identifying each component, or the gel may be divided to provide samples of each component. The components are not bound to the gel, but problems are encountered in encouraging the diffusion of separated components from the gel. The gels are typically cross-linked, insoluble, polyacrylamides but, by using a cross-linking agent including a site capable of selective chemical cleavage, it is possible to solubilise the gel, thus allowing the desired components to diffuse more readily from the gel. The specific sites and cross-linking agents that have been used include: vicinal diols, such as in N,N'-diallyltartardiamide, N,N,N''-triallylcitrictriamide and N,N'-(1,2-dihydroxyethylene) bisacrylamide which may be cleaved with periodate (Tas, J. et al, (1979), Anal. Biochem., 100, 264–270; O'Connell, P.B.H. et al, (1976), Anal. Biochem., 76, 63–73; Anker, H.S., (1970), Febs Lett., 7(3), 293); esters, such as in ethylene diacrylate, which may be cleaved by alkaline hydrolysis (Choules, G.L. et al, (1965), Anal. Biochem., 13, 336–344) and disulphide groups, such as in N,N'-bisacrylylcystamine which may be cleaved with a sulphydryl reducing agent (Hansen, J.N., (1976), Anal. Biochem., 76, 37–44).

There is a need for polymer supports suitable for solid phase peptide synthesis which can also be used directly as carrier molecules for immunisation.

The present invention seeks to provide novel insoluble polymer supports which can be used in peptide synthesis, then the insoluble peptide-polymer conjugates which are formed can be solubilised, and the resulting linear polymer-peptides used in further chemical or biological experimentation in solution.

According to a first aspect of the invention there is provided an insoluble support for use in peptide synthesis comprising an insoluble, cross-linked polymer or copolymer consisting of a soluble polymer or copolymer cross-linked with a cross-linking agent and containing sites for attachment of peptide chains characterised in that the cross-linking agent includes a linkage capable of selective chemical cleavage.

A preferred form of support comprises a cross-linked copolymer of at least one polymerisable monomer which can polymerise to form soluble polymer chains, said at least one polymerisable monomer including a monomer bearing a functionalising group enabling a peptide chain to be covalently attached to the copolymer, and of a cross-linking agent containing a linkage capable of selective chemical cleavage, under conditions which do not cause significant cleavage of peptide bonds or covalent peptide-copolymer linkages, to yield soluble copolymer fragments.

The invention further provides a polymer-peptide conjugate comprising a peptide covalently bound to a polymer wherein the polymer is an insoluble, cross-linked polymer of copolymer consisting of a soluble polymer or copolymer cross-linked with a cross-linking agent characterised in that the cross-linking agent includes a linkage capable of selective chemical cleavage.

The polymer part of such a conjugate is initially in an insoluble form hence providing, for example, a useful insoluble support for a peptide synthesis or for attachment of a peptide synthesised separately or isolated from a biological sample. However, by cleavage of the cross-linking agent, the polymer-peptide conjugate may be rendered in part or wholly soluble. An advantage of this is that a peptide may be synthesised on the insoluble cross-linked polymer support using, for example, the known techniques of solid phase peptide synthesis and the polymer support can then be made soluble by cleaving the cross-linking agent. The soluble polymer-peptide conjugate is then in a form suitable for inoculation, for example as a vaccine.

The polymer-peptide conjugate of the invention is further provided in a soluble form. The soluble form may be in combination with a pharmaceutically acceptable excipient such as a saline solution and may thus be used as a vaccine.

As used herein the term "soluble" means soluble at least under physiological conditions and the term "insoluble" means insoluble at least under the conditions of peptide synthesis.

The soluble polymer may be any polymer or copolymer which may be rendered insoluble by the formation of interchain cross-links. Suitable such polymers include polystrene polydimethylacrylamide, polymethacrylates and the like. The soluble polymer is preferably a polar polymer or copolymer such as a polyamide or a polyacrylamide polymer or copolymer. Particularly preferred is a dimethylacrylamide polymer or a copolymer thereof.

The cross-linking agent comprises a compound having two reactive groups, each capable of bonding to the soluble polymer, the reactive groups being bonded together through a linkage capable of selective chemical cleavage, such that the cross-linking agent, in the insoluble polymer, forms intermolecular bonds between the molecules of the soluble polymer.

As used herein the term "selective chemical cleavage" means that the linkage can be cleaved under conditions which do not otherwise substantially affect the soluble polymer or copolymer. In addition, the conditions should be such that the peptide and any covalent peptide-polymer linkage is not adversely affected. Preferably the linkage is an acid labile linkage. Such linkages are particularly advantageous since the protecting groups commonly used in solid phase peptide synthesis are acid labile and the conditions utilised for peptide synthesis can be selected to include neutral or basic reaction conditions which do not affect acid labile linkages. Thus, having synthesised a peptide on the insoluble polymer, the steps of solubilisation and deprotection can be carried out in a single step.

Where the soluble polymer is one formed by the vinyl polymerisation of one or more unsaturated monomers (for example a polyacrylamide), the cross-linking agent may have the general structure:

$$CH_2=CH-R-CH=CH_2$$

where R is a linkage capable of selective chemical cleavage, preferably acid labile cleavage. Most preferably the cross-linking agent is a compound having the general structure:

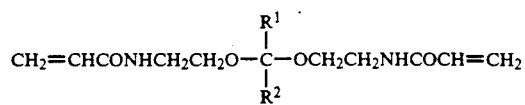

wherein $R^1$ and $R^2$ are the same or different and are selected from hydrogen, alkyl, aryl, aralkyl, alkaryl, alkoxy, and aroxy, provided that wherein $R^1$ is alkoxy or aroxy $R^2$ is not alkoxy or aroxy. Preferably R and $R^2$ are both -H or methyl, the cross-linking agent then being N,N'-bisacryloyl-diaminoethoxymethane or, even more preferably, N,N'-bisacryloyl-2,2-di-)2'-aminoethoxy)propane.

The peptide may be any polypeptide, but is preferably an antigenic or immunodominant polypeptide such as a part of a large polypeptide or protein. Examples of such polypeptides are synthetic peptides which cross-react immunologically with a virus such as foot-and-mouth disease virus, polio virus, influenza virus and hepatitis B virus.

There is further provided a process for the stepwise synthesis of a peptide chain which includes the steps of providing an insoluble polymer support containing pendant functionalising groups to permit attachment of peptide chains and sequentially reacting suitably protected amino acid derivatives therewith to assembly a peptide chain attached to the insoluble polymer support in which there is used an insoluble polymer support according to the invention.

Preferably, such a process includes the further step of subjecting the insoluble polymer support with its attached peptide chain to selective chemical cleavage thereby to effect cleavage of said linkages of said cross-linking agent without significant cleavage of any covalent peptide-polymer bonds or peptide linkages in the peptide chain and to form a solubilised peptide-conjugate.

In a still further aspect of the invention we provide a process for preparing a vaccine capable in vivo of generating antisera to an antigen, comprising synthesising an insoluble polymer-peptide conjugate according to the invention wherein the peptide is capable of immunologically cross-reacting with the antigen, and rendering the insoluble polymer soluble by cleaving the cross-linking agent. The polymer-peptide conjugate may be synthesised by convalently bonding a peptide to the insoluble polymer but, preferably, the peptide is itself synthesised on the insoluble polymer support.

In a further aspect of the invention we provide a method for preparing a vaccine, comprising bringing a soluble polymer-peptide conjugate of the invention into association with a pharmaceutically acceptable excipient, such as a buffer and/or saline solution. We further provide a method for immunising a mammal against an antigen, comprising inoculating the mammal with an effective amount of a soluble form of the polymer-peptide conjugate of the invention, wherein the peptide is a peptide capable of immunologically cross-reacting with the antigen. Also included within the scope of the invention are:

(a) an antibody testing or purification device comprising an insoluble support having absorbed thereon a soluble peptide-polymer conjugate according to the invention, in which the peptide is a specific antigen to the antibody of interest;

(b) a process for purifying antibodies in which a solution containing antibodies of interest is contacted with such a device; and (c) a kit for purifying antibodies comprising an incubation bath for holding a solution containing antibodies and such a device.

As used herein the term "antibody" means any biological molecule including cellular receptor proteins, immunoglobulin-like proteins and nucleic acids, which is capable of binding to or combining with a specific ligand or antigen.

As noted above a preferred insoluble support comprises a cross-linked copolymer of at least one polymerisable monomer which can polymerise to form soluble polymer chains, said at least one polymerisable monomer including a monomer bearing a functionalising group enabling a peptide chain to be convalently attached to the copolymer, and of a cross-linking agent containing a linkage capable of selective chemical cleavage, under conditions which do not cause significant cleavage of peptide bonds or cavalent peptide-copolymer linkages, to yield soluble copolymer fragments. A typcial example of such a support comprises a copolymer of monomers including dimethylacrylamide. The monomer bearing a functionalising group may be a compound containing a protected hydroxyl group, such as an alkylene ester group (e.g. a group of the formula $-(CH_2)_n-CO.OR$, where n is an integer, typcially not more than 8, and R is an alkyl group), capable of undergoing cleavage under mild, preferably basic, reaction conditions, such as by cleavage with ethylene diamine to generate a free hydroxyl group permitting covalent attachment of a peptide by a C-terminal linkage. Examples of such monomers include acryloyl sarcosine methyl ester and 6-acetoxyhexylacrylamide. Preferably the protected hydroxyl group is carried at the end of a chain of at least about 4, and preferably at least about 6 atoms from the polymerisable group of the monomer, e.g. the acrylic radical, so that the deprotected hydroxyl group is separated from the polymer chain backbone. The chain of atoms may include carbon, oxygen and/or nitrogen atoms. 6-acetoxyhexylacrylamide is a momomer of this type.

The ratios of the monomers and cross-linking agent must be selected so as to provide, after selective chemical cleavage, soluble polymer or copolymer chains. In a particularly preferred example an insoluble support for use in peptide synthesis can be produced by copolymerising dimethylacrylamide, N,N'-bisacryloyl-2,2-di-(2'-aminoethoxy)propane and 6-acetoxyhexylacrylamide in a molar ratio of 17.6:1.2:1. This copolymerisation can, for example, be carried out in deoxygenated dimethylformamide solution using benzoyl peroxide (0.3 molar proportion) as initiator.

For ease of handling of the insoluble support of the invention it may be preferred to form the insoluble polymer or copolymer by polymerisation in situ on an inert support, such as kieselguhr, preferably macroporous kieselguhr. In this way a physically supported polymer or copolymer suitable for continuous flow peptide synthesis in a column reactor (A. Dryland and R.C. Sheppard, *J. Chem. Soc. Perkin I*, 1986, 125) can be produced.

As examples of the use of the insoluble polymer support of the invention there will now be described in outline the synthesis of the peptide-polymer conjugates:

(i) H-Arg-Pro-Lys-Pro-Gln-Gln-Phe-Phe-Gly-Leu-Nle-polymer and (ii) H-His-Lys-Thr-Asp-Ser-Phe-Val-Gly-Leu-Met-Gly-polymer where "polymer" represents at each stage of the synthesis either an insoluble polymer or a water soluble polymer chain whose structures will become apparent from the following description. The peptide sequences (i) and (ii) relate respectively to the neuropeptides known as "substance P" and "Substance K" (also known as neurokinin A). Neither of these neuropeptides is intrinsically immunogenic; low concentrations of the free peptides normally circulate in the plasma. These sequences could be assembled on an insoluble polymer support according to the invention, for example a copolymer supported on kieselguhr of dimethylacrylamide, 6-acetoxyhexyl acrylamide and N,N'-bisacryloyl-2,2-di -(2'-aminoethoxy)-propane (hereafter called "polymer A" or "ketal polymer"), using Fmoc-polyamide continuous flow techniques (A. Dryland and R.C. Sheppard, *J. Chem. Soc. Perkin I*, 1986, 125). Another insoluble copolymer support that was used was prepared by copolymerising dimethylacrylamide, N,N'-bisacryloyl-diaminoethoxymethane, and acryloylsarcosine methyl ester (hereinafter called "polymer B" or "formal polymer"). Predominant formation of antibodies directed against the free amino terminal region can be anticipated in the subsequent immunisation schedule and the polymer-bound C-terminal sequence can therefore be modified for ease of synthesis. Formation of the more novel N-terminal antibodies is advantageous in permitting distinction between tachykinins with identical C-terminal sequences.

After removal of the protecting acetyl groups from the residues of the 6-acetoxyhexyl acrylamide monomer in the insoluble polymer A support with diaminoethane, the first amino acid residue was esterified to the resin using the Fmoc-amino acid anhydride in the presence of dimethylaminopyridine to react with the deprotected hydroxyl group. Subsequent residues were added as Fmoc-amino acid pentafluorophenyl esters of the formula

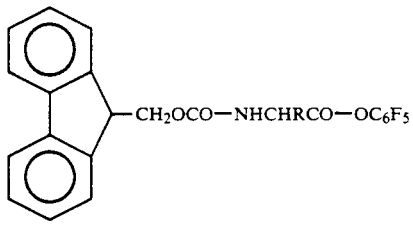

(A. Dryland and R.C. Sheppard, *Tetrahedron*, 1988, 44, 859) in the presence of anhydrous 1-hydroxylbenzotriazole catalyst in the case of peptide-polymer conjugate (i), or the corresponding 3-(3,4-dihydro-4-oxo-benzotriazinyl) esters of the formula

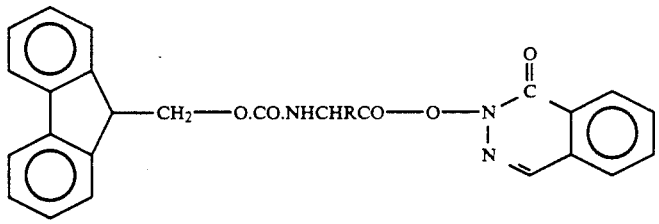

(E. Atherton, L.R. Cameron, M. Meldal, and R.C. Sheppard, *J. Chem. Soc. Chem. Comm.*, 1986, 1763), in the case of peptide-polymer conjugate (ii). Anhydrides were used in place of the non-crystalline esters of Fmoc-O-t-butyl-serine and threonine. t-Butyl ethers, esters, of t-butoxycarbonyl derivatives were used for amino acid side chain protection as appropriate. Arginine was protected as the 4-methoxy-2,3,6-trimethylbenzene sulphonyl (Mtr) derivative. Use of base-labile fluorenylmethoxycarbonylamino acid derivatives throughout avoids the acidic reaction conditions of conventional solid phase synthesis. In the absence of water, no evidence was obtained for significant dissolution of the polymer by weakly acidic species (such as hydroxybenzotriazole or pentafluorophenol) present in the reaction mixtures. The insoluble peptide-polymer conjugate (ii) was solubilised, "side chain" deprotected, and separated from insoluble kieselguhr support by treatment with 95% aqueous trifluoroacetic acid for 90 minutes. Deprotection of arginine-containing peptide-insoluble polymer conjugate (i) was extended overnight in the presence of phenol (cleavage of the Mtr-group). Both peptide-polymer A conjugate preparations (i) and (ii) were freely water soluble after this treatment; the substance K related polymer eluted in the void volume on gel permeation chromatography (Sephadex G75), suggesting a molecular weight in excess of 50,000. Somewhat more difficulty was experienced in solubilising the corresponding peptide-polymer B conjugates than their polymer A counterparts.

In these experiments, fidelity of synthesis was confirmed by ammonolysis of the soluble peptide-polymer at the carboxy terminal ester linkage, gel filtration from the linear polymer, and hplc characterisation and amino acid analysis (Found: Arg, 1.01; Pro, 2.04; Lys, 1.02; Glu, 2.10; Phe, 1.94; Gly, 1.04; Leu. 1.00; Nle, 1.02 for (i) and His, 0.93; Lys; 0.98; Thr, 0.99; Asp, 1.01; Ser, 0.86; Phe, 0.97; Val, 1.00; Leu, 1.00; Met, 0.94; Gly, 2.01 for (ii)).

All the peptide-polymer conjugates described above are immunogenic in rabbits. Both the formal and ketal substance P-polymers (i.e. The solubilised substance-P formal polymer conjugate and the solubilised substance P-ketal polymer conjugate) produce useful antibody titers, better than 1:500 and comparable t those elicited by a conventional substance P-bovine serum albumin conjugate at similar points in the immunisation schedule. Antibodies to substance P can be detected using peptide labelled at the amino terminus with $^{125}$I-Bolton-Hunter reagent. Antibodies to Substance K can be detected using the blotting procedure described below.

A valuable application of the invention is to provide a novel product, which is convenient to handle, that comprises an insoluble support having absorbed thereon a soluble peptide-polymer conjugate according to the invention. Such a product can be used to isolating antibodies specific to a peptide antigen from an antiserum containing a multiplicity of antibodies. An example of the use of such a product will now be described.

The peptide-polymer conjugates absorbed onto nitrocellulose membranes were incubated with the peptide antisera. The sites of antibody binding were detected using sheep anti-rabbit IgG antisera and rabbit peroxidase-anti-peroxidase complex with diaminobenzidine as the chromogen (L.A. Sternberger, *Immunocytochemistry*, 3rd Edn. Prentice Hall, New York, 1986). This procedure detected antibodies to substance P and substance K in sera from rabbits immunised respectively with the substance P and substance K-polymers. Less than 1 ng of peptide-polymer bound to nitrocellulose was detectable, and under these conditions the polymer itself gave no response. Blots of the peptide polymer conjugates were also detected by anti-peptide antibodies raised conventionally using the appropriate synthetic peptides coupled to protein.

The general principle of using in solid phase synthesis insoluble gel supports which can then be solubilised and further manipulated in free solution appears to be a valuable one. In application similar to the above, detachment of efficiently synthesised peptides may not normally be required, and it provides an exceptionally rapid and simple procedure for generating immunogens. It has particular potential for the economic large scale production of peptide vaccines. Those skilled in the art will appreciate that it will provide a valuable tool in immunochemical research.

The invention is now illustrated, by way of example only, by the following Examples, which refer to the accompanying drawings, in which.

EXAMPLE 1

Polymer Preparation

Figure 1:
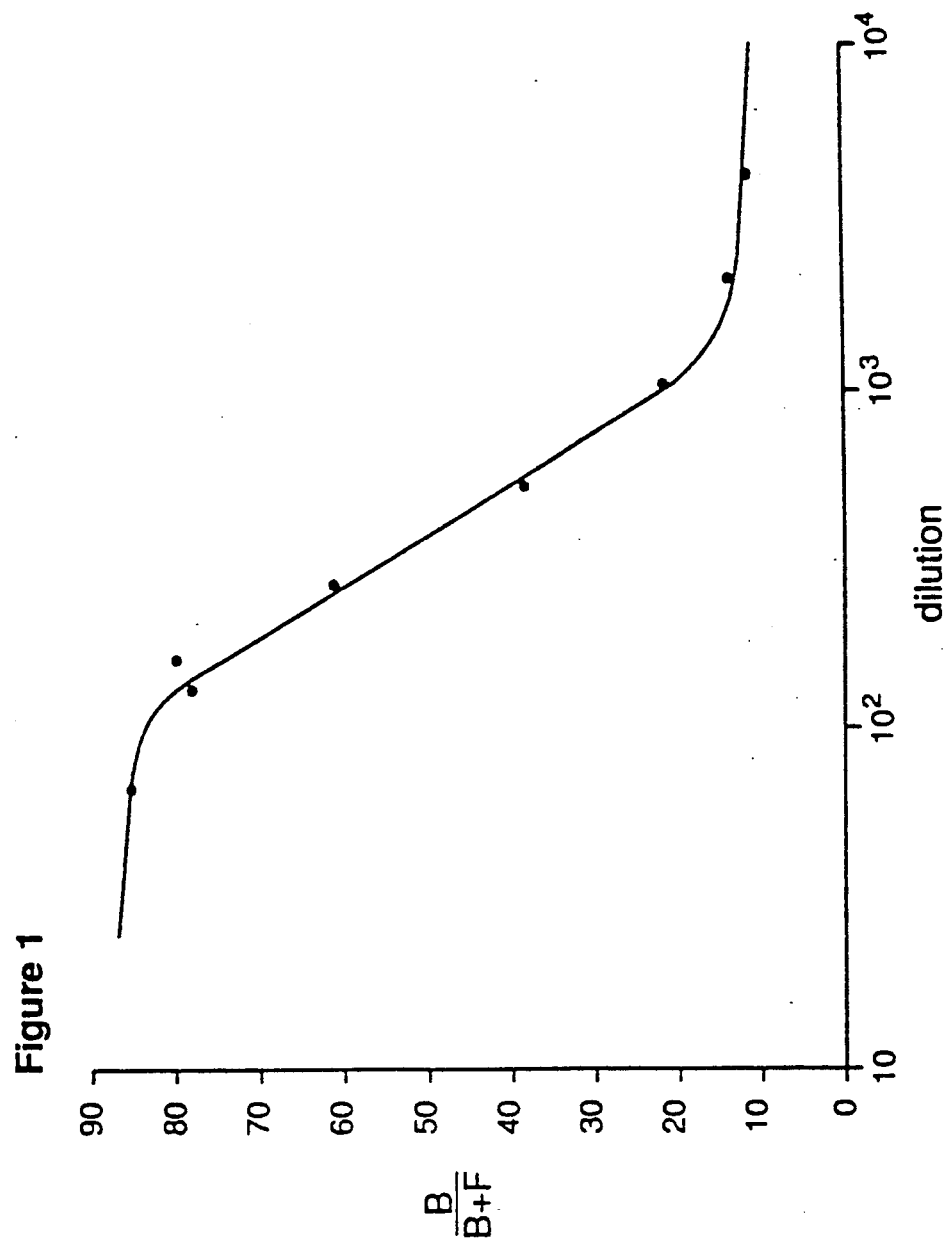
FIG. 1 shows the binding of substance P (labelled with $I^{125}$) with an IgG fraction of an antisera raised using a polymer-peptide conjugate of the invention.

The polymer was prepared as a beaded gel resin by modification of the procedure of R. Arshady, E. Atherton, D.L.J. Clive, and R.C. Sheppard, *J. Chem. Soc., Perkin I,* 1981, 529. N,N'-Bisacryloyl-diaminoethoxymethane was incorporated into the polymer in place of the normal cross-linking agent, N,N'-bisacryloyl-1,2-diaminoethane.

Preparation of
N,N'-bisacryloyl-diaminoethoxymethane

Anhydrous chloroform (51 cm³) was added to a flask containing diaminoethoxymethane (10 g, 74.6 mmol), prepared as described by R.F. Webb, A.J. Duke, and L.S.A. Smith *J. Chem. Soc.,* 1962, 4307–4319, and anhydrous sodium acetate (13.60 g, 163 mmol). The mixture was stirred with a magnetic stirrer and cooled to 0° C. in an ice water bath. Distilled acryloyl chloride (13.59 g, 150 mmol) was added dropwise during 1 h. Once the addition was complete ca 0.1 g hydroquinone was added to the mixture and this was refluxed for 35 minutes and then allowed to cool. Water (200 cm³) was added and the organic phase was removed and retained. Sodium chloride was added to the aqueous phase which was extracted exhaustively with chloroform. The combined chloroform extracts were dried ($Na_2SO_4$) and evaporated. The product was recystallised from hot ethyl acetate and dried in vacuo to give a white crystalline solid; yield 14.55 g (80%), m.p. 104°–105° C., tlc (silica) in ethyl acetate-acetone (1:1 v/v), $R_f$ 0.39, nmr, δ ($CDCl_3$, 60 MHz) 3.6 (8 H, multiplet, $CH_2CH_2O$), 4.6 (2 H, singlet, $OCH_2O$), 5.5 (2 H, multiplet, $CH_2=CHCO$), 6.1 (4 H, multiplet, $CH_2=CHCO$), 6.7 (2 H, singlet, $=CHCONH$), Found: C 54.63, H 7.39, N 11.32. $C_{11}H_{18}N_2O_4$ requires C 54.53, H 7.49, N 11.56%.

Suspension Polymerisation

Cellulose acetate butyrate (Eastman, 17% Butyryl, ASTM Viscosity 15) (6.25) was completely dissolved in freshly distilled dichloroethane (150 cm³) and placed in a cylindrical fluted polymerisation vessel fitted with a stirrer and nitrogen inlet and maintained at 50±1° C. in a thermostatically controlled water bath. The solution was stirred at 450 ±20 rpm and flushed with $N_2$ for 15 minutes prior to addition of the monomer mixture which consisted of dimethylacrylamide (7 g, 70.6 mmol), acryloyl sarcosine methyl ester (1.5 g, 9.37 mmol) and N,N'-bisacryloyl-diaminoethoxymethane (1.26 g, 5.20 mmol), diluted with cooled (5° C.) dimethylformamide-water (1:2), (75 cm³) and mixed well with ammonium persulphate (1.125 g). Polymerisation was allowed to continue under a slow stream of nitrogen for ca. 15 h when the mixture was cooled, diluted with acetone-water (1:1 v/v), stirred until a homogeneous suspension was obtained, and filtered. The recovered polymer was further washed with dimethylformamide and any fine particles removed by decantation. Finally, the polymer was washed with diethyl ether and dried ($P_2O_5$) in vacuo; yield 7.7 g of beaded resin (Found: Sar, 0.78 mequiv. g⁻¹).

The polymer is readily obtained in a well beaded form using the suspension polymerisation technique described above. Variation in the amount of acryloyl sarcosine methyl ester in the copolymiersation mixture enables the preparation of resins with variable functionality. In addition to the 0.78 mequiv. $g^{-1}$ resin, a resin with a much lower sarcosine content (0.23 mequiv. $g^{-1}$) has also been prepared. This incorporates twice the amount of N,N'-bisacryloyl-diaminoethoxymethane to limit the degree of swelling of the final resin. Generally, the higher the crosslink density of a copolymer the less it will swell in a given solvent system. Thus not only can the functionality of the resin be varied but the likely swelling characteristics can also be controlled.

For peptide synthesis it is not necessary to use a bead polymer. The new polymer is also amenable to preparation by a method of copolymerisation within the pores of a fabricated kieselguhr support. The general procedure has been described by E. Atherton, E. Brown, R.C. Sheppard, and A. Rosevear, *J. Chem. Soc., Chem. Comm.,* 1981, 1151 for a polymer incorporating the original crosslinking agent, N,N'-bisacryloyl-1,1-diaminoethane.

Solid Phase Synthesis of
Des-Amido-[11-Nle]-Substance P-Polymer

BOC.Arg.Pro.Lys(BOC)Pro.Gln.Gln.Phe.Phe.Gly.Leu.Nle-Resin
1                     10

The dimethylacrylamide-N,N'-bisacryloyl-diaminoethoxymethane-acryloylsarcosine methyl ester copolymer (0.5 g) was shaken with re-distilled ethylene diamine (20 cm³) overnight at room temperature. The resin was washed thoroughly with DMF (10×1 min), 10% diisopropylethylamine in DMF (3×1 min) and DMF (10×1 min). The amino-resin was acylated with fluorenylmethoxycarbonyl (FMOC)-Nle-pentafluorophenyl ester, prepared as described by E. Atherton and R.C. Sheppard, *J. Chem. Soc., Chem. Comm.,*

1985, 165 (1.0 mmol, 60 min), and the FMOC group cleaved with 20% piperidine-DMF. The incorporation of norleucine was 0.6 mequiv. $g^{-1}$.

The resin was swollen in DMF and one half by volume was removed. The remaining half was retained in the reaction cell and used for the synthesis of substance P using a modified Beckman 990 Peptide Synthesiser (see E Atherton, C.J. Logan, and R.C. Sheppard, *J. Chem. Soc., Perkin Trans. I.,* 1981, 538). For the coupling reactions the FMOC-amino-acids were activated as their pentalfuorophenyl esters (Leu, Gly, Phe and Pro) or p-nitrophenyl esters (Gln and Lys(BOC)). The p-nitrophenyl esters were coupled in the presence of the catalyst, hydroxybenzotriazole, an equivalent amount of which was added to the reaction mixture. Each activated FMOC-amino acid (0.5 mmol) in DMF (ca 4.5 cm$^3$) was added in sequence to the deprotected peptide-resin. The coupling reactions, judged qualitatively by ninhydrin and 2,4,6-trinitrobenzene sulphonic acid tests, were complete within ca 60 mins. To complete the synthesis, BOC.Arg(HCl)-OH (2.4 mmol) was preactivated with dicyclohesylcarbodiimide (1.2 mmol) in DMF (5 cm$^3$) for 5 min. and the whole reaction mixture was added to the resin. It was convenient to leave the acylation overnight.

Samples for amino acid analysis were removed after addition and deprotection of residues 4 (Phe), 6 (Gln), 9 (Lys), and 11 (Arg).

| Step | 4 | 6 | 9 | 11 |
| --- | --- | --- | --- | --- |
| Nle | 0.97 | 0.97 | 0.97 | 0.97 |
| Leu | 1.00 | 0.99 | 1.00 | 1.00 |
| Gly | 1.00 | 1.00 | 1.00 | 1.00 |
| Phe | 1.02 | 2.06 | 2.05 | 2.06 |
| Gln |  | 1.01 | 2.06 | 2.03 |
| Pro |  |  | 0.97 | 1.92 |
| Lys |  |  | 0.91 | 0.92 |
| Arg |  |  |  | 0.91 |

The final peptide-resin was washed thoroughly with DMF and diethyl ether and dried in vacuo to give 0.323 g of resin with a peptide loading of 0.33 mmol $g^{-1}$. (Potentially 104.6 μmol of peptide).

EXAMPLE 2

Solubilisation Experiments

Gel Resin

90% Aqueous trifluoroacetic acid (TFA) (7 cm$^3$) was added to the beaded gel polymer (Sar, 0.78 mequiv. $g^{-1}$) (50 mg) causing it to swell, but not dissolve. When the mixture was shaken vigorously at room temperature for 24 hours the polymer did dissolve to give a clear homogeneous solution. This was evaporated to dryness to give a glass. Water (7 cm$^3$) was added and after further shaking (6 h) a viscous solution was formed. The pH of the solution was adjusted to pH 7.0 with base. A sample (0.5 cm$^3$) was applied to a Sephadex G25 column (83×2.5 cm) packed and eluted in water and was found to be eluted at the void volume (molecular weight>5,000).

A sample of the high load H-Nle-Resin (0.6 mmol $g^{-1}$) (ca 15 mg) prepared as described in Example 1 was shaken with neat TFA (10 cm$^3$) for 24 hours at room temperature. The solution was filtered to remove a small amount of insoluble material and the filtrate evaporated to dryness. The residue was easily dissolved in water (2.0 cm$^3$) to give a solution containing 7.7 μmol Nle (90% recovery). A sample of this solution was applied to a Sephadex G50 column (87×2.5 cm) packed and eluted in water, and was found to be eluted at the void volume (molecular weight>30,000).

EXAMPLE 3

Des-amido-[Nle]-Substance P-Polymer

A solution of 95% aqueous TFA containing 10% v/v resorcinol (20 cm$^3$) was added to the protected substance P-(Nle)-Resin (20 mg) prepared as described in Example 1. The resin became swollen and the mixture was shaken vigorously for 48 hours at room temperature. Evaporation of the viscous solution gave a white solid which was washed with diethyl ether (2×3 cm$^3$). Water (30 cm$^3$) was added to the sticky residue and the mixture shaken at room tempetature overnight. The aqueous frothy solution was filtered to remove some insoluble gel and the filtrate was collected and lyophilised to give a white powder which was largely dissolved in diethyl ether (2 cm$^3$). The remaining gelatinous solid was easily dissolved in water (3 cm$^3$) and the solution (pH 7.0) was applied to a Sephadex G50 column (87×2.5 cm) packed and eluted in water. The eluent was monitored continuously at 210 nm and was collected by a fraction collector. Fractions eluting between 107-250 cm$^3$ (Vo=152 cm$^3$) were combined and concentrated in vacuo. The residual solution was lyophilised to give a white solid which readily redissolved in water (3cm$^3$) to form a slightly viscous solution, PG 3/52. By amino acid analysis the peptide-polymer solution, PG 3/52, contained 0.88 μmol peptide (1.15 mg), Arg (0.89), Lys (0.90), Pro (1.85), Gln (2.03), Phe (2.09), Gly (1.00), Leu (0.98), Nle (0.96). The solution was used directly in subsequent immunological studies.

The insoluble gel isolated in the initial aqueous filtration step was retained and lyopohilised to give a white solid (13 mg) which was analysed by amino acid analysis and found to contain 3.37 μmol (4.48 mg) peptide; Arg (0.89), Lys (0.93), Pro (1.94), Gln (2.04), Phe (2.07), Gly (1.00), Leu (0.98), Nle (0.97). The solid was gelled in 2 cm$^3$ water and this was used directly in immunological studies.

EXAMPLE 4

Immunological Studies

Figure 2:
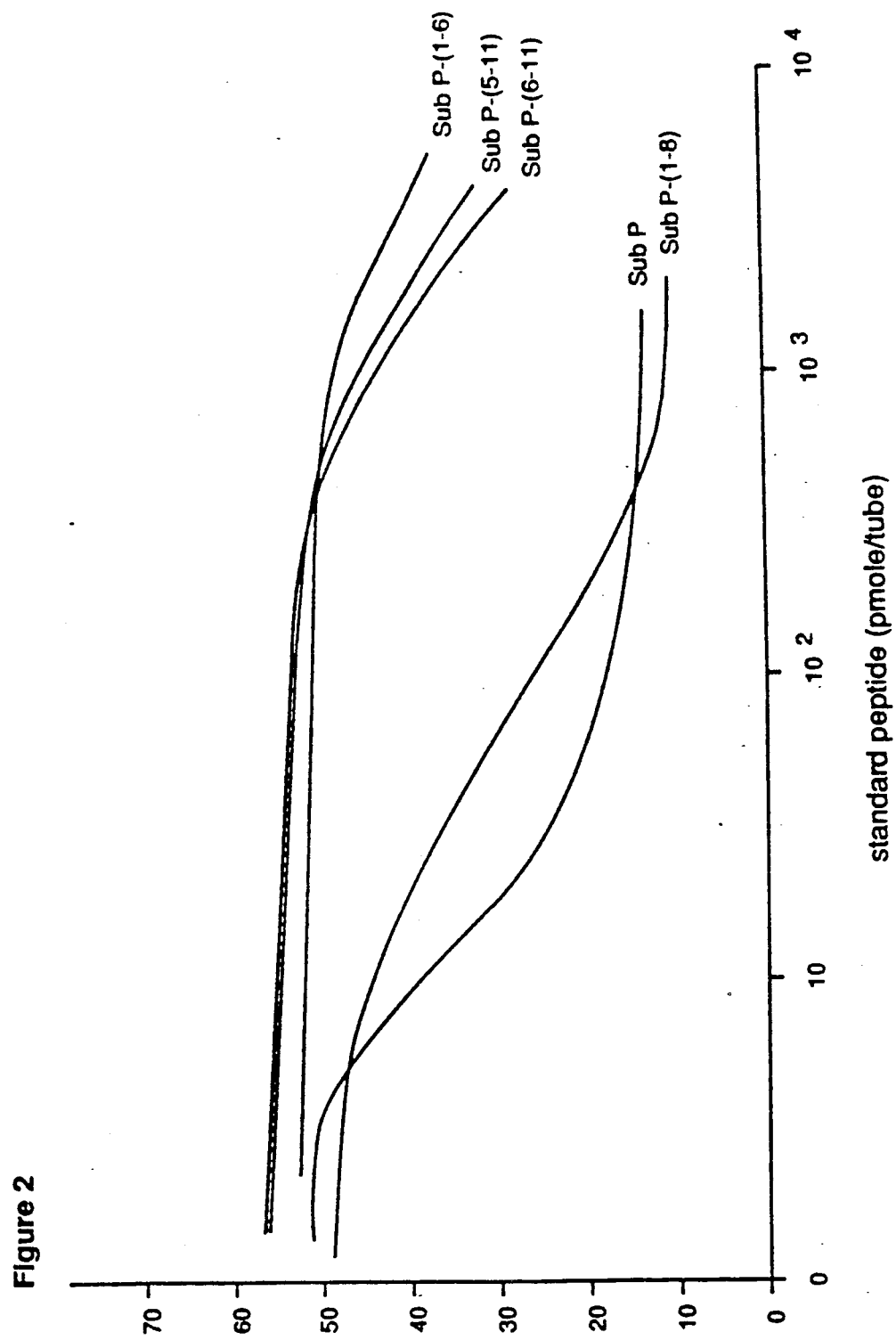
FIG. 2 shows the cross-reactivity of the antiserum with substance P fragments.

Dutch belted rabbits were immunised with the peptide-polymer solution PG3/52 (1.15 mg peptide dissolved in 3 cm$^3$ water) prepared as described in Example 3. The animals received a 1.0 cm$^3$ injection of PG3/52 (0.5 cm$^3$) emulsified with 0.5 cm$^3$ of complete Freunds adjuvant (DIFCO). Injections were made intravenously into the hindquarters. Subsequent injections were made at four week intervals but after the initial immunisation, the peptide-polymer solution was emulsified with incomplete Freunds adjuvant. The rabbits were bled by the ear vein after two immunisations and the serum fraction (2.5 cm$^3$) tested for its ability to bind I$^{125}$-Bolton-Hunter substance P tracer (5,000 cpm). Tracer binding was detectable after three immunisations and reached a titre plateau of 1:400 in the best rabbit. As a result of this low titre an immunoglobulin fraction (IgG) was prepared by an ammonium sulphate fractionation and DEAE cellulose chromatography. This confirmed that the antibody produced a conventional IgG fraction and gave an unambiguous tracer binding and antibody dilution curve (FIG. 1). Characterisation of the antiserum with substance P analogues (FIG. 2) showed that the antiserum recognised substance P and substance P-(1-8), but displayed only a poor affinity for the smaller amino-terminal fragment substance P-(1-4) and the carboxyl-terminal analogues substance P-(5-11) and substance P-(6-11). This implies as would be expected that the antiserum was directed towards the amino-terminus of substance P. The related peptide, substance K (neurokinin A) which has a completely different amino-terminus did not cross react with the antiserum even at a thousand fold molar excess.

EXAMPLE 5

Preparation of 6-hydroxyhexylacrylamide

6-Aminohexanol (4.50 gm, 38.4 mmole) was dissolved in a solution of 27.5 gm of $Na_2CO_3 \cdot 10H_2O$ and 50 ml of acetone in 150 mL of water. This solution was cooled in an ice bath. A solution of 3.43 mL of acryloyl chloride (42.2 mmole) in 30 mL of acetone was added dropwise over a period of 40 minutes. The reaction proceeded one hour in the ice bath and 30 minutes at room temperature. The solvents were removed in vacuo until the solution was saturated in $Na_2CO_3$. The solution was then extracted with $5 \times 25$ mL of ethyl acetate. The organic extracts were combined and dried over $Na_2SO_4$. After filtration and evaporation the crude yield was 5.81 gm. The residue was extracted with several portions of boiling ether. After evaporation the yield was 4.84 gm: (28.3 mmole, 73%) mp 58°-59° C. TLC $R_f$ 0.22 ($CHCl_3$:MeOH, 9:1). Analysis $C_9H_{17}NO_2$ requires C, 63.13%; H, 10.00%; N, 8.18%. Found: C, 63.19%; H, 9.71%; N, 8.04%.

Preparation of 6-acetoxyhexylacrylamide

6-Hydroxyhexylacrylamide (4.00 gm, 23.4 mmole), acetic anhydride (4.41 mL, 46.8 mmole) and dimethylamino pyridine (23.3 mg, 2.3 mmole) were dissolved in 15 mL of pyridine and were allowed to react at room temperature for 4 hours. After evaporation of the solvents the residue was dissolved in 100 mL of ethyl acetate and was washed with N HCl and brine. After drying over $Na_2SO_4$ the organic solution was filtered and the solvent was removed in vacuo to yield a yellow syrup. Crystallisation was induced by adding and evaporating benzene followed by hexane. Crude yield: 4.84 gm, mp 38°-45° C. 3.5 gm of this crude product was dissolved in 20 mL of EtOAc, decolorised with charcoal and was dropped into 200 mL of hexane. On stirring the material crystallised. After sitting at 4° C. overnight the product was collected. Yield 2.50 gm (71% recrystallised) mp 43°-43.5° C. TLC $R_f$ 0.47 ($CHCl_3$:MeOH 9:1). NRM:$\delta(CDCl_3)$ 6.67 (br s, 1 H, NH), 5.5-6.4 (M, 3 H, $CH_2=CH-$), 4.03 (tr, J=6 Hz, 2 H, $CH_2O$) 3.30 (br q, 3 H, $CH_2N$), 2.02 (s,3 H, $COCH_3$), 1.4 (m, 8 H, $(CH_2)_4$). Analysis: $C_{11}H_{19}NO_3$ requires C, 61.95%; H, 8.98%; N, 6.56%. Found: C, 62.09%; H, 9.09%; N, 6.51%.

Preparation of 2,2-di-(2-phthalimidoethoxy)propane

A solution of 50.0 gm of hydroxyethyl phthalimide (0.26 mole) in 200 mL of benzene was slowly distilled through a 10 inch column of glass helices to remove traces of $H_2O$. After cooling, 16 mL of 2,2-dimethoxy propane (0.13 mmole) and 15 mg of para-toluenesulfonic acid were added to the benzene solution. The mixture was brought to reflux and the benzene-methanol azeotrope distilled over at 55° C. When the head temperature rose abruptly TLC showed the reaction to be complete so 5 mL more of 2,2-dimethoxy propane was added. Distillation was continued until 40 mL of distillate in total was collected. The reaction was neutralised with ammonia in benzene and was filtered hot. The benzene was evaporated in vacuo and the residue was dried under vacuum: 53.9 gm of crude product. This material was recrystallised from 300 mL of ethyl acetate to give 22.1 gm of white crystals: 0.054 mole, 41%. mp 139°-141° C. NMR $\delta(CDCl_3)$ 7.50 (m, 8 H, aromatic CH), 3.33 (m, 8 H, $NCH_2$), 1.23 (s, 6 H, geminal $(CH_3)_2$). TLC, $R_f$ 0.48 ($CHCl_3$:MeOH 98:2).

Preparation of 2,2-di-(2-aminoethoxy)propane 2,2-Di-(2-phthalimidoethoxy)propane (46.2 gm, 0.11 mole), sodium hydroxide (43.7 gm, 1.10 mole) and 100 mL of $H_2O$ were combined and refluxed for 20 hours. After cooling this solution was extracted with p-dioxane in a liquid-liquid extractor for 20 hours. The p-dioxane was removed by rotary evaporation to give a yellow oil. The oil was distilled under reduced pressure yielding 12.5 gm of a clear colourless oil: 0.077 mole, 71%. bp 107°-110° C./0.18 mm Hg. NMR $\delta(CDCl_3)$ 3.41(tr, 4 H, J=6 Hz, $CH_2O$), 2.78(tr, 4 H, J=6 Hz, $NCH_2$), 1.33 (s, 6 H, geminal $(CH_3)_2$), 1.20(s, 4 H, $NH_2$).

Preparation of N,N'-bisacryloyl-2,2-di-(2-aminoethoxy)propane 2,2-Di-(2-aminoethoxy)propane (11.0 gm, 67.8 mmole) was dissolved in a solution of 450 mL of 0.67 sodium carbonate and 130 mL of acetone and was cooled in an ice bath. Acryloyl chloride (18.1 mL, 223 mmole) dissolved in 150 mL of acetone was added dropwise and the solution stirred overnight. The acetone and water were evaporated in vacuo until the solution was saturated in salts. The solution was then extracted with $6 \times 50$ mL of chloroform. The chloroform extracts were combined, dried over sodium sulphate, filtered and the solvent was removed in vacuo to yield a syrup. Crystals were formed on addition of benzene. After evaporation 14.6 gm of crude product was obtained. This material was recrystallised from ethyl acetate and hexane to give 13.1 gm of white crystals: 48.6 mmole, 72%. mp 94°-95° C. NMR $\delta(CDCl_3)$ 7.0 (br s, 2 H, NH), 5.7-6.5 (m, 4 H, $=CH_2$), 5.50 (tr, 2 H, -CH=), 3.47 (m, 8 H, $NCH_2CH_2O$), 1.30 (s, 6 H, geminal $(CH_3)_2$). Analysis: $C_{13}H_{22}N_2O_4$ requires C, 57.76%; H, 8.20%; N, 10.36%. Found: C, 57.79% H, 8.18%; N, 10.29%.

Preparation of Kieselguhr Supported Copoly(Dimethylacrylamide-6-acetoxyhexylacrylamide-N,N'-bisacryloyl-2,2-di-(2-aminoethoxy)propane Dimethylacrylamide (3.35 gm, 33.8 mmole), 6-acetoxyhexylacrylamide (0.409 gm, 1.92 mmole) and N,N'-bisacryloyl-2,2-di-(2-aminoethoxy)propane (0.627 gm, 2.32 mmole) were dissolved in 8 mL of DMF and $N_2$ gas was bubbled through the solution for 15 minutes. Concurrently $N_2$ gas was bubbled through a solution of 0.530 gm of benzoyl peroxide (2.19 mmole) in 5 mL of DMF for 15 minutes. After $N_2$ deoxygenation, the monomer solution and 2.5 mL of the initiator solution were mixed and placed in a dropping funnel with a pressure equalising tube. The dropping funnel was fitted onto a 100 mL round bottom flask containing 10 gm of kieselguhr. The system was evacuated by means of a water aspirator pump for 5 minutes. The solution was then dropped into the kieselguhr in one portion. With the pump still operating the apparatus was picked up and shaken gently to ensure an even distribution of solution in the kieselguhr. After 3 minutes of shaking the apparatus was closed to the vacuum and $N_2$ was allowed in. The flask of the apparatus was submerged in a 60° C. water bath for 20 minutes. After 17 hours at room temperature the product was collected on a sinter and was washed with DMF and 0.05 M Tris (aq). The material ws then forced through a 700 μm sieve using hand pressure and washing with 0.05 M Tris. The beads were collected and the fines were removed by decantation using 0.05 M Tris. The resin was then washed with DMF and $Et_2O$ and was dried over $SiO_2$ under vacuum. Yield: 11.84 gm. Polymer content 22.2%.

EXAMPLE 6

Synthesis of Des-amido-[11-Norleucine]-Substance-P-Polymer

The kieselguhr supported copolymer of dimethyl acrylamide, 6-acetoxyhexylacrylamide, and N,N'-bisacryloyl-2,2-di -(2-aminoethoxy)propane (1.10 gm) was shaken with neat diaminoethane overnight. After washing with DMF the resin was placed in a reaction column on a benchtop model continuous flow synthesiser (see Dryland, A.D., Sheppard, R.C., J. Chem. Soc. Perkin Trans. I 1986 125–137) and washed further with DMF until the effluent was negative to ninhydrin. The resin was then acylated with 0.38 mmole of the symmetrical anhydride of 9-fluorenylmethoxycarbonyl norleucine (Fmoc-Nle-OH). The anhydride was prepared by dissolving 0.282 gm of Fmoc-Nle-OH (0.8 mmole) in 10 mL of dichloromethane and adding 0.0784 gm of dicyclohexylcarbodiimide (0.38 mmole). After 20 minutes the dicyclohexylurea was filtered off and the solvent was evaporated in vacuo. The residue was taken up in 1 mL of DMF, applied to the resin and was allowed to soak into the bed. Dimethylaminopyridine (DMAP, 0.022 gm, 0.1 mmole) in 0.5 mL of DMF was added. The reagents were recirculated through the system and the acylation proceeded for 60 minutes. After washing out the resin it was re-acylated in an identical manner with the amounts of $(Fmoc-Leu)_2O$ and DMAP. The resin was capped with 0.4 mmole of acetic anhydride and 0.1 mmole of DMAP. The peptide was then elaborated with successive cycles of Fmoc deprotection with 20% piperidine and acylation with 1.5 mL solutions of 0.4 mmoles of the appropriate $N^\alpha$-Fmoc-amino acid Dhbt ester (Atherton, E, Cameron, L.R., Meldal, M., and Sheppard, R.C., J. Chem. Soc. Chem. Comm., 1986, 1763). Couplings were judged to be complete when both the Kaiser ninhydrin test (Kaiser, E.; Colescott, R.C.; Bossinger, C.D.; Cook, P.I., Analyt, Biochem., 34, 595 (1970)) and the trinitrobenzenesulfonic acid test (Hancock, W.S.; Battersby, J.E., Analyt, Biochem., 71, 261 (1976)) were negative. The side chain amino group of lysine was protected with the Boc group. Arginine was added as the symmetric anhydride of FmocArg(Mtr)OH. At the completion of the syntheses the Fmoc group from the N-terminal arginine was removed and the resin was washed with DMF and ether. After drying over KOH in high vacuum for 24 hr the kieselguhr supported substance-P-polymer conjugate was stored at −20° C. until needed for deprotection and solubilisation. Yield 1.06 gm. Amino Acid Analysis: Arg (0.87) Pro (1.80) Lys (0.89) Gln (1.99) Phe (2.02) Gly (1.02) Leu (1.00) Nle (1.17). Loading: 0.056 mmole of leucine/gm of kieselguhr resin. Organic content of resin: 29.9%.

EXAMPLE 7

Solubilisation—Deprotection of the Substance-P-Polymer Conjugate

Kieselguhr supported protected substance-P-polymer conjugate, 0.20 gm, prepared as described in Example 6, was treated with trifluoroacetic acid: phenol 95:5 (v/w), plus a trace of water, for 17 hours. After filtration the trifluoroacetic acid was removed by rotary evaporation. Water was added and evaporated in vacuo. The residue was dissolved in 20 mL of $H_2O$ and organic by products were removed by partitioning with diethyl ether. After evaporating the water the residue was dissolved in 0.1 M acetic acid, to a final volume of 5.3 mL, 0.1 mL was taken for amino acid analysis. The remainder was passed through a Sephadex G-25 column: dimensions, 2.5×88.5 cm; solvent, 0.1 M acetic acid; flow rate, 1.0 mL/min; 10 mL fractions. The high molecular weight peak was collected and lyophilised. After drying for 24 hours in high vacuum over $P_2O_5$ and KOH the weight was 25.9 mg. This was dissolved in 2.2 mL of $H_2O$. Amino acid analysis of this solution indicated a leucine content 165 μmole of leucine/gm of substance-P-polymer, 1.94 μmole of leucine/mL. This solution was stored at −20° C. until needed for immunological testing.

EXAMPLE 8

Synthesis of Substance-K-Glycine-Polymer

The kieselguhr supported copolymer of dimethylacrylamide, 6-acetoxyhexylacrylamide, and N,N'-bisacryloyl-2,2-di -(2-aminoethoxy)propane, 1.5 gm, was treated with neat diaminoethane overnight. It was washed extensively with DMF and ether and dried under vacuum over KOH for 1 hour. A suspension of 1.2 gm of the dried resin in DMF was placed in a reaction column in a benchtop continuous flow peptide synthesiser. The resin was then acylated with 0.38 mmole of the symmetric anhydride of Fmoc-glycine in an analogous manner to the initial acylation described in the substance-P-polymer synthesis. After capping with acetic anhydride the peptide was elaborated by successive cycles of Fmoc-deprotection using 20% peperidine in DMF for 10 minutes and acylation using 0.4 mmoles of the appropriate $N^\alpha$-Fmoc-amino acid-pentafluorophenyl ester in 1.5 mL of DMF plus 0.1 mmole of anhydrous HOBt. The HOBt was made anhydrous by dissolving it in absolute ethanol and evaporating in vacuo twice followed by suspending in anhydrous benzene and evaporating in vacuo two times. Fmoc-Ser-(OtBu)-OH and Fmoc-Thr(OtBu)-OH were added as symmetric anhydrides. The side chains of histidine and lysine were protected with the Boc group, threonine and serine were protected as t-butyl esters, and glutamic acid was protected as the t-butyl ester. Usually couplings were complete within 20 minutes, as judged by the ninhydrin trinitrobenzenesulphonic acid tests. The exception was histidine which required an overnight coupling time. After removal of the Fmoc group from the N-terminal histidine the resin was washed with DMF and ether and it was dried in high vacuum over KOH for 24 hours. The kieselguhr supported substance-K-polymer conjugate was stored at −20° C. until needed for solubilisation and deprotection. Yield: 1.00 gm.

Amino Acid Analysis: His (0.79) Lys (0.81) Thr (0.96) Asp (1.01) Ser (0.96) Phe (0.90) Val (0.90) Gly (2.02) Leu (1.00) Met (0.89). Loading: 0.055 mmoles of leucine/gm of kieselguhr supported resin. Organic content of resin: 28.1%.

EXAMPLE 9

Solubilisation and Deprotection of the Substance-K-Polymer Conjugate

Kieselguhr supported substance-K-polymer conjugate, 0.100 gm, prepared as described in Example 8, was treated with 5 mL of 95% TFA for 90 minutes. The kieselguhr was removed by filtration and washed with 5 mL of TFA. The TFA was evaporated from the combined filtrate and washings to yield a clear, colourless gum. This was dissolved in 5 mL of 0.1 M acetic acid and was washed with ether. 0.1 mL was taken for amino acid analysis. The remainder of the aqueous solution was passed down a Sephadex G-25 column: dimensions, 2.5×88.5 cm; solvent, 0.1 M acetic acid; flow rate, 1.0 mL/min; 10 minute fractions. The high molecular weight peak was collected and lyophilised. After drying in high vacuum over KOH and $P_2O_5$ for 24 hours the weight was 23.3. mg. Amino acid analysis of the final product showed 204 μmole of leucine/gm of substance-K-polymer conjugate. The product was dissolved in 2 mL of $H_2O$ + 5μl of acetic acid and was frozen at −20° C. until needed for immunological testing.

Solubilisation—Deprotection of the Substance-K-Polymer Conjugate

Kieselguhr supported substance-K-polymer conjugate, 0.116 gm, was treated with 10 mL of TFA:$H_2O$ (95:5) for 90 minutes. The kieselguhr was filtered off and washed with 10 mL of TFA. The TFA from the combined filtrate and TFA washings was evaporated in vacuo and the resulting oil was dissolved in 5.0 mL of 0.1 M acetic acid. This solution of the aqueous phase was extracted with 3×2.5 mL of ether. The volume was then 4.6 mL, and 0.25 mL was removed for amino acid analysis. The remainder of the solution was passed down a Sephadex G-25 column: dimensions: 35.5×2.5 cm; solvent, 0.1 M acetic acid; flow rate, 1.0 mL/min; 5 minute fractions. Fractions containing product were pooled, lyophilised, and dried over KOH in high vacuum for 24 hours. Yield: 13.1 mg. This was dissolved in 5 mL of $H_2O$ and 0.25 mL was taken for amino acid analysis. The amino acid analysis showed a leucine content of 260 μmole leu/gm-peptide-polymer conjugate, 0.67 μmole of leucine/mL. The solution was frozen at −20° C. until needed for immunological testing.

EXAMPLE 10

Binding of Antibodies by Peptide-Polymer Conjugate Blotted onto Nitrocellulose Membrane Samples of peptide-polymer conjugate containing the equivalent of 0.1 ng to 10 μg of peptide in 20 μL were blotted onto a nitrocellulose membrane. After drying the blots the membrane was soaked in phosphate buffered saline containing 3% BSA (PBS/BSA) for one hour at 37° C. The membranes were washed in PBS/BSA and then soaked in 5 mL of a 1:100 dilution of rabbit antipeptide antiserum in PBS/BSA for one hour at 37° C. After washing in PBS the membranes were soaked for ½ hr in a 1:50 dilution of sheep antirabbit-IgG serum in PBS. The membranes were washed in PBS and soaked in rabbit anti-peroxidase-peroxidase complex for ½ hr at 37° C. After washing in PBS blots were visualised by covering the membranes in 0.1% diamino benzidine in PBS and adding ca 1 μl of 30% $H_2O_2$.

EXAMPLE 11

Ability of Peptide-Polymer Conjugates to Elicit Antibody Production

Figure 3:
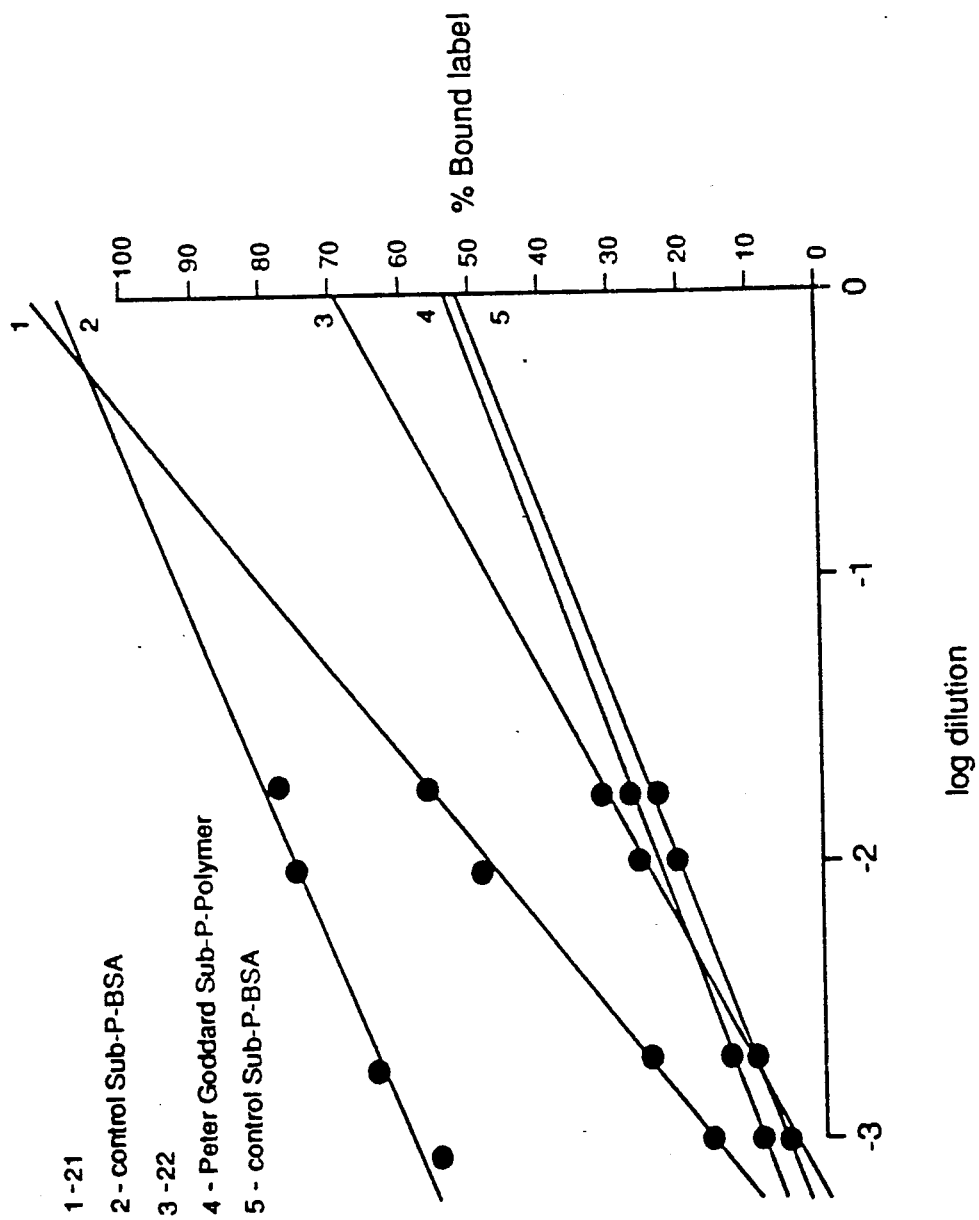
FIG. 3 shows the binding of free, labelled substance P by antiserum to three different antigens.

Both substance-K-polymer solution of Example 9, and substance-P-polymer solution of Example 7, were tested for their ability to raise anti-peptide antibodies in Dutch Belted rabbits. FIG. 3 shows the binding of free, labelled substance-P by antisera raised against three different antigens: (1). The substance-P-polymer synthesised on the kieselguhr supported resin (rabbits 21 and 22), (2). The substance-P-polymer conjugate synthesised on the unsupported, beaded resin (1 rabbit) and (3). Substance-P-BSA conjugate (2 rabbits). The rabbits had been immunised with conjugate equivalent to 200 ng of substance-P emulsified in complete Freunds adjuvant, boosted at 2 weeks and 6 weeks with the same amount in incomplete Freunds adjuvant and bled at 8 weeks. Substance-P-polymer was immunogenic in Dutch Belted rabbits and elicited an antibody titer comparable to that of conventional substance-P-BSA conjugate (FIG. 3 and Table 1). The same strain of rabbits also produced an antibody response against substance-K polymer, which was detected using the nitrocellulose blotting test.

TABLE 1

Testing of the Binding of $^{125}$I-labelled Substance-P by Antisera Raised Against Various Antigens

| Antigen | % Binding of $^{125}$I-Substance-P to antibody[a,b] serum dilution | | | |
|---|---|---|---|---|
| | 1:50 | 1:100 | 1:500 | 1:2000 |
| Substance-P-polymer JSM1-343B, Rabbit 21 | 57.3[c] | 50.6 | 28.5 | 16.9 |
| Substance-P-polymer JSM1-343B, Rabbit 22 | 33.2 | 26.5 | 11.1 | 5.3 |
| Substance-P-polymer P.G. | 29.2 | 24.6 | 13.5 | 10.5 |
| Substance-P-BSA | 78.2 | 76.2 | 65.4 | 56.1 |
| Substance-P-BSA | 27.0 | 22.4 | 10.5 | 7.8 |

[a]diluted serum was incubated with substance-P labelled with $^{125}$I-Bolton-Hunter Reagent. Charcoal was added and the mixtures were centrifuged. B = counts in supernatant (antibody bound), F = counts in pellet (free substance-P).
[b]% Binding = B/(B + F)
[c]% Binding is the average of two values.

EXAMPLE 12

The Ability of the Peptide-Polymer Conjugate to Bind Antibodies Raised against Peptide-KLH Conjugates and Peptide-polymer conjugates Affinity purification of antipeptide antibody can be accomplished by blotting a peptide polymer conjugate (such as one of the peptide-polymer conjugates used in Example 11) onto a nitrocellulose membrane and placing it in contact with the antisera. Such peptide-polymer conjugates adhere quite strongly to nitrocellulose membranes. Antisera raised against peptide-KLH conjugates were used. In the case of substance-P the carboxy terminus of the peptide was bound to KLH so the antibodies were directed against the N-terminus. For the substance-K-KLH complex the antibodies were directed against the C-terminus. However both substance-P-polymer and substance-K-polymer were able to bind antibody raised against their respective KLH counterparts. Antibody binding to substance-P-polymer equivalent to about 1 ng of substance-P was detected. Antibody binding to substance-K-polymer containing 0.1 ng of substance-K was detected. The same blotting procedure was used to detect the presence of anti-peptide antibodies in rabbits immunised with the peptide-polymer conjugates. Three rabbits immunised with substance-K-polymer produced antibodies which were detectable on substance-K-polymer blots containing 0.1 ng of substance-K. Rabbit 21, which was immunised with substance-P-polymer produced antibodies which were detectable on substance-P-polymer produced blots containing 1 ng of substance-P. Nitrocellulose blots of peptide-polymer conjugates provide a facile method of detecting antipeptide antibodies and hence provide a novel method of affinity purifying those antibodies.

EXAMPLE 13

Figure 4:
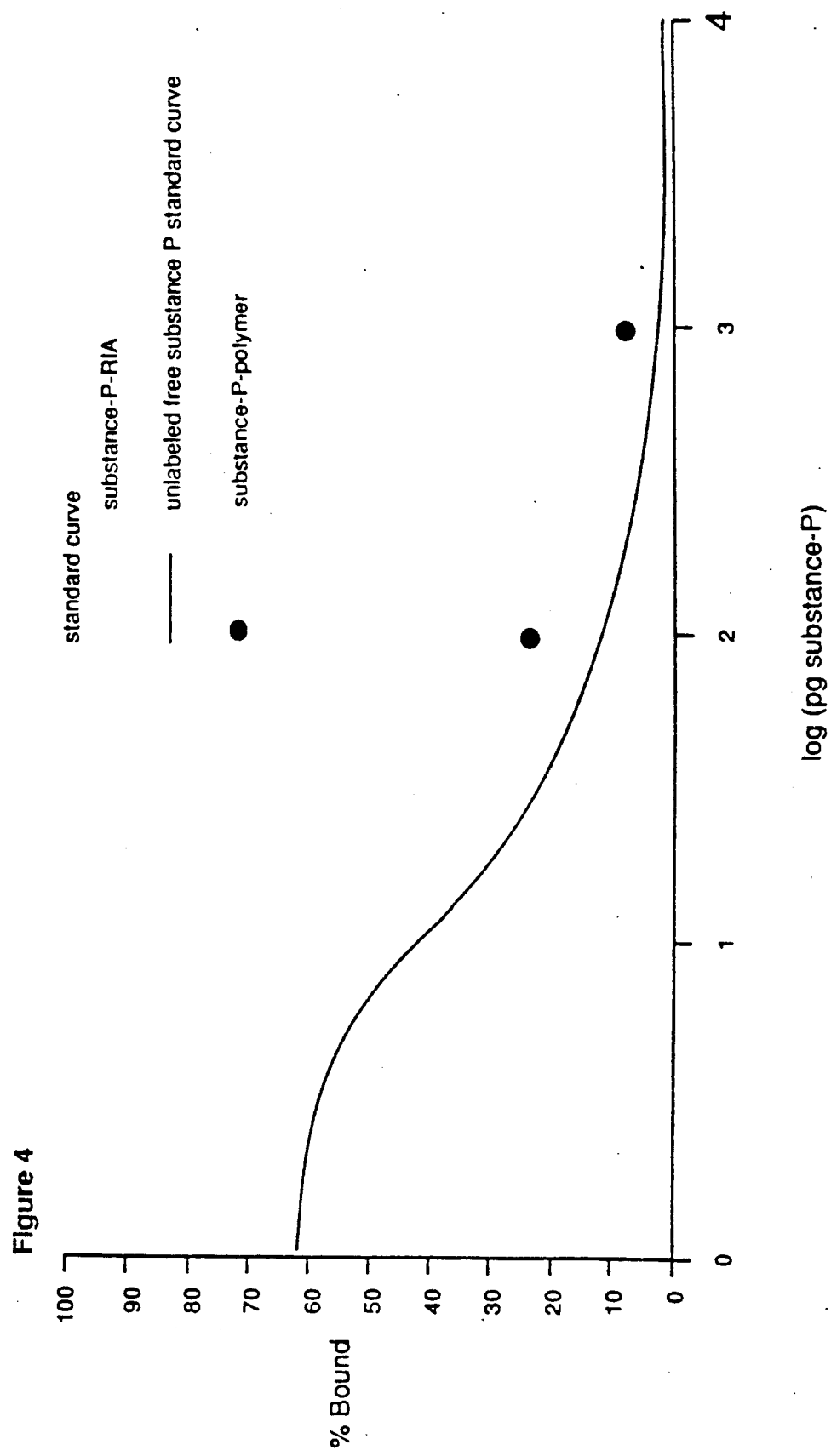
FIGS. 4 and 5 show the ability of polymer bound peptide to compete with free peptide in a radioimmunoassay fluid.

The Ability of Polymer Bound Peptide to Compete with Free Peptide in a Radioimmunoassay The same antisera that were used in the blotting assay of Example 12 were used in the radioimmunoassay (RIA). As can be seen from FIG. 4, two concentrations of substance-P-polymer gave a response in the readable portion of the standard curve of the substance-Px RIA. The amount of peptide-polymer corresponding to 92.6 pg and 1.01 ng of substance-P gave the same degree of competition as did 39 and approximately 400 pg of unlabelled, unbound substance-P respectively. Thus the antibody raised against N-terminal free substance-P-KLH could effectively bind approximately 40% of the polymer bound substance-P.

Figure 5:
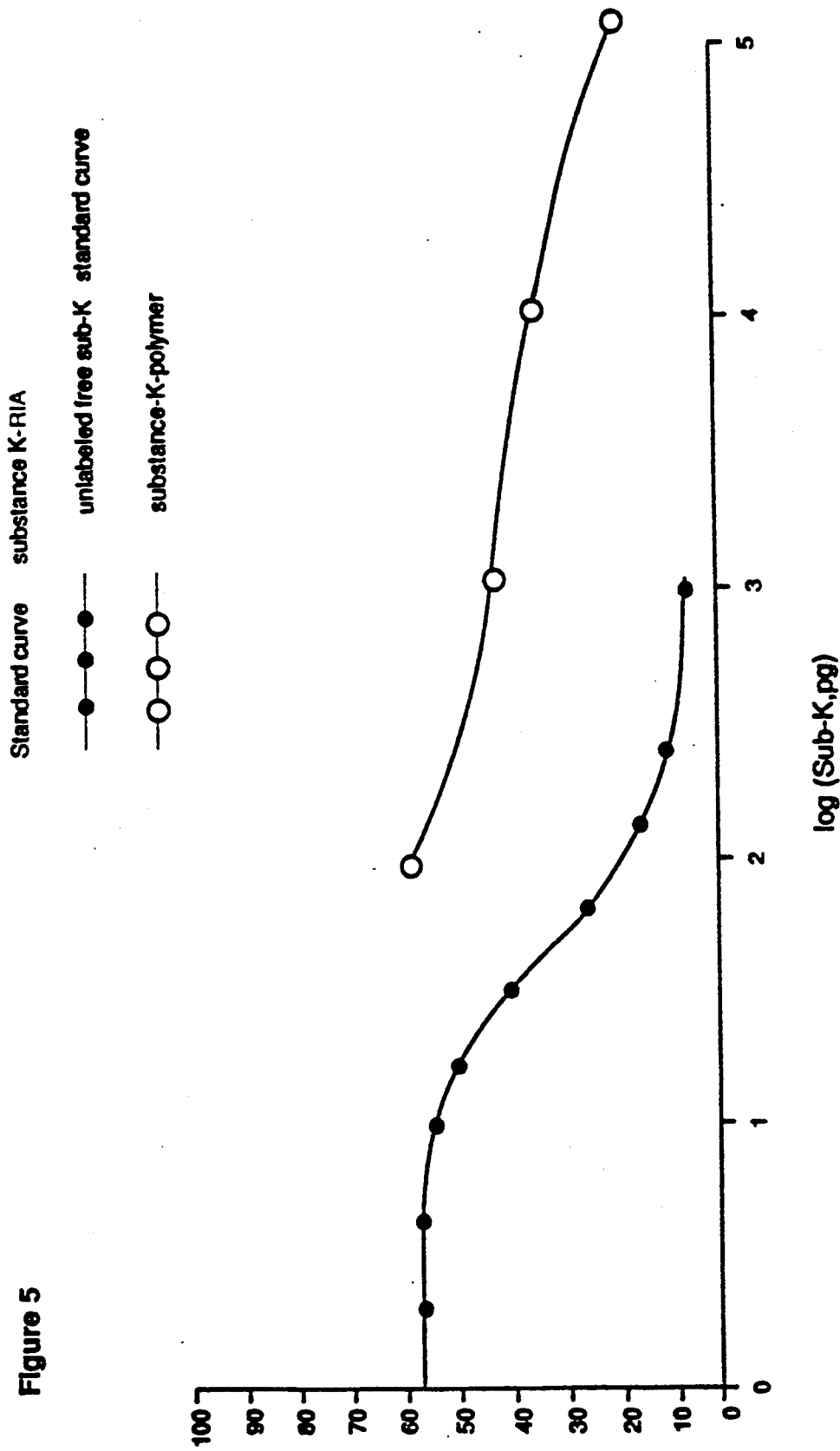

Substance-K-polymer did not compete well with free substance-K in the RIA (FIG. 5). This is not surprising considering the antibodies were directed against the carboxy terminus of the peptide, which is bound to the polymer in the conjugate. The antibody response to a particular antigen is polyclonal, and the fact that substance-K-polymer did show a certain degree of competition indicates that there is at least one antibody capable of binding to the interior of the peptide.

EXAMPLE 14

Isolation of Anti-peptide Antibodies using a Polymer-peptide Conjugate

Preparation of the Polymer-Peptide Conjugate

The peptide sequence H-Asp.Asp.Flu.Val.Asp.Gly OH which corresponds to residues 2-6 of endoplasmin (+glycine as linker) was prepared using the LKB Biolynx peptide synthesis system. The polymer used was that described in Example 6. The yield of polymer-peptide was 44 mg and the weight of associated peptide was 8.3 mg corresponding to 0.189 g peptide/g of polymer-peptide conjugate. The amino acid analysis yielded Gly (1) Val (0.91) Asp (2.88) and Glu (0.96). The conjugate was dissolved in 5 ml of water and incubated with a strip (5 sq cm) of nitrocellulose paper (Schleicher and Schuell) at 4° C. for 2 hours. The strip was then blocked with gelatin solution (1% in water for 30 minutes) and mixed for 48 hours with a rabbit anti-serum raised to the amino terminal (17 residue) sequence of endoplasmin.

The strip was then eluted with 2 ml of 0.2 M with 1 M Tris base to pH 6.8. The purified antibody was tested by immunoblotting with endoplasmin which gave a strong specific reaction, showing that the polymer-peptide conjugate bound to nitrocellulose could efficiently entrap antibodies which reacted with a corresponding peptide sequence. No reaction was obtained with proteins lacking an endoplasmin amino acid sequence in the polymer-peptide conjugate.

We claim:

1. A polymer-peptide conjugate comprising an insoluble polymer support having at least one peptide chain covalently linked thereto, said insoluble polymer support consisting of a soluble polymer or copolymer cross-linked by residues of a cross-linking agent which contains a linkage capable of selective chemical cleavage, under selected cleavage conditions which do not cause significant cleavage of peptide bonds or of the covalent peptide-polymer support linkages by means of which said at least one peptide chain is convalently linked to said insoluble polymer support, whereby upon submission of said polymer-peptide conjugate to said selected cleavage conditions said polymer-peptide conjugate can yield soluble peptide-polymer or peptide-copolymer fragments.

2. A polymer-peptide conjugate according to claim 1, in which said insoluble polymer support comprises a cross-linked copolymer of (i) at least one polymerisable monomer which can polymerise to form soluble polymer chains, said at least one polymerisable monomer including a monomer bearing a functionalising group enabling a peptide chain to be covalently attached to the copolymer, and (ii) a cross-linking agent containing a linkage capable of selective chemical cleavage, under conditions which do not cause significant cleavage of peptide bonds or covalent peptide-copolymer linkages, to yield soluble peptide-polymer or peptide-copolymer fragments.

3. A polymer-peptide conjugate according to claim 2, in which the monomer bearing a functionalising group is a compound containing a protected hydroxyl group capable of cleavage to generate a free hydroxyl group permitting covalent attachment of a peptide by a C-terminal linkage.

4. A polymer-peptide conjugate according to claim 3, in which the monomer bearing a functionalising group comprises 6-acetoxyhexylacrylamide.

5. A polymer-peptide conjugate according to claim 1, in which said insoluble polymer support comprises a copolymer of monomers including dimethylacrylamide.

6. A polymer-peptide conjugate according to claim 1, in which the cross-linking agent comprises a compound of the general structure

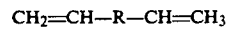

$CH_2=CH-R-CH=CH_3$ where R is a linkage capable of selective chemical cleavage.

7. A polymer-peptide conjugate according to claim 6, in which R is a linkage capable of selective chemical cleavage under acidic conditions.

8. A polymer-peptide conjugate according to claim 7, in which the cross-linking agent is a compound having the general structure

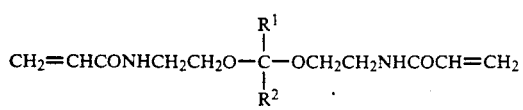

wherein $R^1$ and $R^2$ are the same or different and are selected from hydrogen, alkyl, aryl, aralkyl, alkaryl, alkoxy, and aroxy, provided that, where $R^1$ is alkoxy or aroxy, $R^2$ is not alkoxy or aroxy.

9. A polymer-peptide conjugate according to claim 8, in which $R^1$ and $R^2$ are both H, the cross-linking agent then being N,N'-bisacryloyl-di-2-aminoethoxymethane.

10. A polymer-peptide conjugate according to claim 1, in which the cross-linking agent is N,N'-bisacryloyl-2,2'-di-(2'-aminoethoxy-propane.

11. A polymer-peptide conjugate according to claim 1, in which said insoluble polymer support is formed in situ on an inert carrier.

12. A polymer-peptide conjugate according to claim 11, in which the inert support comprises kieselguhr.

13. A polymer-peptide conjugate comprising a peptide chain covalently bound to an insoluble, cross-linked polymer or copolymer cross-linked with a cross-linking agent which includes a selectively cleavable linkage capable of selective chemical cleavage under selected chemical cleavage conditions which do not cleave any peptide linkage or covalent linkage linking said peptide chain to said insoluble, cross-linked polymer or copolymer whereby, upon submission of said polymer-peptide conjugate to said selected chemical cleavage conditions, said selectively cleavage linkage is cleaved to release soluble polymer-peptide fragments comprising a polymer or copolymer chain having at least one peptide fragment covalently linked thereto and being soluble under physiological conditions.

14. A process for the production of a solubilised peptide-polymer conjugate which comprises the steps of:
providing an insoluble polymer support containing pendant functionalising groups to permit attachment of peptide chains to said insoluble polymer support and comprising an insoluble, cross-linked polymer or copolymer consisting of a soluble polymer or copolymer cross-linked with a cross-linking agent which includes a selectively cleavable linkage capable of cleavage under selective chemical cleavage conditions which do not cause cleavage of peptide bonds or of covalent linkages between peptide chains and said insoluble polymer support;
sequentially reacting with said functionalising groups on said insoluble polymer support a plurality of protected amino acid derivatives in turn thereby to build up stepwise through attachment to said functionalising groups at least one peptide chain attached through a covalent linkage to said insoluble polymer support; and
subjecting said insoluble polymer support with its attached peptide chains to said selective chemical cleavage conditions thereby to effect cleavage of said selectively cleavable linkages without significant cleavage of any covalent peptide-polymer bonds or peptide linkages in the polymer chains and to form a solubilised polymer-peptide conjugate comprising a soluble polymer or copolymer chain having at least one peptide chain covalently attached thereto.

15. A process according to claim 14, in which the step of sequentially reacting said protected amino acid derivatives with said insoluble polymer support is effected under neutral or basic reaction conditions and in which said selective chemical cleavage conditions include use of acidic conditions.

16. A process according to claim 14, in which said insoluble polymer support comprises a cross-linked copolymer of (i) at least one polymerisable monomer which can polymerise to form soluble polymer chains, said at least one polymerisable monomer including a monomer bearing a functionalising group enabling a peptide chain to be covalently attached to the copolymer, and (ii) a cross-linking agent containing a linkage capable of selective chemical cleavage, under conditions which do not cause significant cleavage of peptide bonds or covalent peptide-copolymer linkages, to yield soluble copolymer fragments.

17. A process according to claim 16, in which said cross-linked copolymer is a copolymer of monomers including a compound containing a protected hydroxyl group capable of cleavage to generate a free hydroxyl group permitting covalent attachment by a C-terminal group of a peptide, which protected hydroxyl group has then been subjected to hydroxyl group deprotection to cause deprotection of said protected hydroxyl group.

18. A process according to claim 17, in which the monomer containing a functionalising group comprises 6-acetoxyhexylacrylamide.

19. A process according to claim 16, in which said cross-linked copolymer comprises a copolymer of monomers including dimethylacrylamide.

20. A process according to claim 14, in which the cross-linking agent comprises a compound of the general structure $$CH_2=CH-R-CH=CH_2$$

where R is a linkage capable of selective chemical cleavage.

21. A process according to claim 20, in which R is a linkage capable of selective chemical cleavage under acidic conditions.

22. A process according to claim 21, in which the cross-linking agent is a compound having the general structure

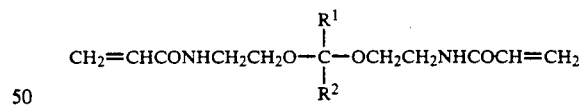

where $R^1$ and $R^2$ are the same or different and are selected from hydrogen, alkyl, aryl, aralkyl, alkaryl, alkoxy, and aroxy, provided that, wherein $R^1$ is alkoxy or aroxy, $R^2$ is not alkoxy or aroxy.

23. A process according to claim 22, in which $R^1$ and $R^2$ are both H, the cross-linking agent then being N,N'-bisacryloyl-di-2-aminoethoxymethane.

24. A process according to claim 14, in which the cross-linking agent is N,N'-bisacryloyl-2,2'-di-(2'-aminoethoxy)-propane.

25. A process according to claim 14, in which said plurality of protected amino acid derivatives comprises at least one Fmoc-amino acid pentafluorophenyl ester.

26. A process according to claim 14, in which said insoluble polymer support is formed in situ on an inert carrier.

* * * * *